US010023846B2

(12) United States Patent
Nishie et al.

(10) Patent No.: US 10,023,846 B2
(45) Date of Patent: Jul. 17, 2018

(54) PRODUCTION METHOD FOR NON-ENVELOPED VIRUS PARTICLES (71) Applicant: TAKARA BIO INC., Shiga (JP)

(72) Inventors: Toshikazu Nishie, Moriyama (JP); Yasuhiro Kawano, Machida (JP); Shuhei Sakamoto, Moriyama (JP); Tatsuji Enoki, Kyotanabe (JP); Hikaru Takakura, Kyoto (JP); Junichi Mineno, Uji (JP)

(73) Assignee: TAKARA BIO INC., Shiga (JP)

( * ) Notice: Subject to any disclaimer, the term of this patent is extended or adjusted under 35 U.S.C. 154(b) by 0 days.

(21) Appl. No.: 15/323,811

(22) PCT Filed: Jul. 9, 2015

(86) PCT No.: PCT/JP2015/069770
§ 371 (c)(1),
(2) Date: Jan. 4, 2017

(87) PCT Pub. No.: WO2016/006658
PCT Pub. Date: Jan. 14, 2016

(65) Prior Publication Data
US 2017/0166871 A1 Jun. 15, 2017

(30) Foreign Application Priority Data
Jul. 10, 2014 (JP) ................. 2014-142200

(51) Int. Cl.
C12N 7/00 (2006.01)
(52) U.S. Cl.
CPC ...... C12N 7/00 (2013.01); C12N 2750/14151 (2013.01)
(58) Field of Classification Search
None
See application file for complete search history.

(56) References Cited

U.S. PATENT DOCUMENTS

| 5,043,357 A | 8/1991 | Hoffler et al. |
| 2007/0275449 A1 | 11/2007 | Wu et al. |
| 2008/0118970 A1 | 5/2008 | Konz, Jr. et al. |
| 2008/0132688 A1 | 6/2008 | Zhou |
| 2009/0275107 A1 | 11/2009 | Lock et al. |
| 2011/0027399 A1 | 2/2011 | Shimamoto et al. |
| 2016/0152955 A1 | 6/2016 | Sakamoto et al. |
| 2016/0273058 A1 | 9/2016 | Akashika et al. |
| 2017/0166871 A1* | 6/2017 | Nishie ............... C12N 7/00 |

FOREIGN PATENT DOCUMENTS

| CN | 101173300 | 5/2008 |
| CN | 102205132 | 10/2011 |
| CN | 102260651 | 11/2011 |
| EP | 0 245 949 | 11/1987 |
| EP | 2 871 239 | 5/2015 |
| JP | 63-14702 | 1/1988 |
| JP | 2001-145496 | 5/2001 |
| JP | 2012-529917 | 11/2012 |
| WO | 97/06272 | 2/1997 |
| WO | 97/08298 | 3/1997 |
| WO | 97/17458 | 5/1997 |
| WO | 00/14205 | 3/2000 |
| WO | 02/12455 | 2/2002 |
| WO | 2008/109686 | 9/2008 |
| WO | 2009/123183 | 10/2009 |
| WO | 2010/148143 | 12/2010 |
| WO | 2011/074564 | 6/2011 |
| WO | 2014/007120 | 1/2014 |

OTHER PUBLICATIONS

Wolf and Reichl (Expert Review of Vaccines. 2011; 10(10): 1451-1475).*
Zhou et al. (Journal of Virological Methods. 2011; 173: 99-107).*
Office Action dated Jun. 28, 2017 in U.S. Appl. No. 14/900,837.
Vandenberghe et al., "Efficient Serotype-Dependent Release of Functional Vector into the Culture Medium During Adeno-Associated Virus Manufacturing", Human Gene Therapy, 21(10):1251-1257 (2010).
Lock et al., "Rapid, Simple, and Versatile Manufacturing of Recombinant Adeno-Associated Viral Vectors at Scale", Human Gene Therapy, 21(10):1259-1271 (2010).
Zolotukhin et al., "Recombinant adeno-associated virus purification using novel methods improves infectious titer and yield", Gene Therapy, 6(6):973-985 (1999).
Sokol et al., "Purification of Rabies Virus Grown in Tissue Culture", Journal of Virology, 2(8):836-849 (1968).
Advisory Action dated Oct. 30, 2017 in U.S. Appl. No. 14/900,837.
Schagen et al., "Ammonium sulphate precipitation of recombinant adenovirus from culture medium: an easy method to increase the total vims yield", Gene Therapy, 2000, vol. 7, No. 18, pp. 1570-1574.
Office Action dated Dec. 22, 2017 in U.S. Appl. No. 14/900,837.
Taylor, A. C., "Responses of Cells to pH Changes in the Medium", Journal of Cell Biology, 1962, vol. 15, pp. 201-209.
Safaiyan et al., "Selective Effects of Sodium Chlorate Treatment on the Sulfation of Heparan Sulfate", Journal of Biological Chemistry, 1999, vol. 274, No. 51, pp. 36267-36273.
Venkatakrishnan, B., "Endosomal Ph Mediated Structural Transitions in Adeno-Associated Viruses", University of Florida, Doctoral Dissertation, 2012, pp. 1-132.
Extended European Search Report dated Dec. 18, 2017 in European Patent Application No. 15819589.1.
International Preliminary Report on Patentability dated Jan. 10, 2017 in corresponding International Application No. PCT/JP2015/069770.

(Continued)

Primary Examiner — Shanon A Foley
(74) Attorney, Agent, or Firm — Wenderoth, Lind & Ponack, L.L.P.

(57) ABSTRACT

Provided are a production method for non-enveloped virus particles which is characterized in that a sample including non-envelopes virus particles is treated with PEG in at least two concentrations; a kit used in said production method; non-enveloped virus particles produced using said production method; and a pharmaceutical composition having the non-envelopes virus particles as an active ingredient.

10 Claims, 3 Drawing Sheets

(56) References Cited

OTHER PUBLICATIONS

Guo et al., "A simplified purifica ion method for AAV variant by polyethylene glycol aqueous two-phase partitioning", Bioengineered, 4(2):103-106 (2013).
Guo et al., "Rapid and simplified purification of recombinant adeno-associated virus", J Virol Methods, 183(2):139-146 (2012).
International Search Report dated Oct. 14, 2014 in International Application No. PCT/JP2014/068438.
International Preliminary Report on Patentability dated Jan. 12, 2016 in International Application No. PCT/JP2014/068438.
Gencoglu et al., "Porcine parvovirus flocculation and removal in the presence of osmolytes", Journal of Biotechnology, 186:83-90 (2014).
Greenhalgh et al., "Virus Clearance in Your Process from Start to Finish", BioProcessing Journal, 12(4):48-52 (2013).
Dos Santos Coura et al., "A role for adeno-associated viral vectors in gene therapy", Genetics and Molecular Biology, 31, 1, 1-11 (2008).
Morenweiser, "Downstream processing of viral vectors and vaccines", Gene Therapy, 12:S103-S110 (2005).
Extended European Search Report dated Feb. 9, 2017 in European Application No. 14823074.1.
Takimoto et al., "Effect of Hypochlorite-Based Disinfectants on Inactivation of Murine Norovims and Attempt to Eliminate or Prevent Infection in Mice by Addition to Drinking Water", Exp. Anim., 62(3):237-245 (2013).
Yokoyama et al., "Removal of small non-enveloped viruses by nanofiltration", Vox Sanguinis, 86(4):225-229 (2004).
Office Action dated Nov. 7, 2016 in U.S. Appl. No. 14/900,837.
International Search Report dated Oct. 6, 2015 in corresponding International Application No. PCT/JP2015/069770.
Office Action dated Oct. 10, 2017 in corresponding Chinese patent application No. 201480039156.9, with English translation.
Office Action dated Jan. 25, 2017 in corresponding Chinese patent application No. 201480039156.9, with English translation.
Office Action dated May 3, 2018 in Chinese Application No. 201480039156.9, with English translation.
Communication pursuant to Article 94(3) EPC dated May 9, 2018 in European Application No. 14823074.1.

* cited by examiner

PRODUCTION METHOD FOR NON-ENVELOPED VIRUS PARTICLES

TECHNICAL FIELD

The present invention relates to a method of producing a non-enveloped virus particle with high purity and with no laborious operation.

BACKGROUND ART

In the field of gene recombination or the field of medicine, for introduction of a gene into cells of mammals including human, physical methods using electroporation or metal microparticles, chemical methods using nucleic acid, polycation, or liposome, and biological methods using vectors for gene transfer wherein viruses are used as the vectors (hereinafter, referred to as viral vectors) have been currently used. The viral vectors mean vectors obtained by altering natural viruses so that the viruses can transfer a desired gene or the like into a target, and the development of such vectors has been recently advanced. Vectors prepared by gene recombination technology are usually called recombinant viral vectors. Well-known examples of viruses which the recombinant viral vectors are derived from include viruses with envelopes, for example retrovirus, lentivirus, Sendai virus, and herpes virus, and viruses without envelopes (non-enveloped viruses), for example adenovirus, and adeno-associated virus (hereinafter, referred to as AAV).

In particular, AAV can infect a wide variety of cells including human cells, and AAV infects even non-dividing cells in which differentiation terminates, including blood cells, muscle cells, and nerve cells. In addition, since AAV is not pathogenic to human, it has a low risk of adverse effect. The virus particle of AAV is physicochemically stable. For these reasons, AAV has recently attracted attention to utility value as a vector for gene transfer used in gene therapy for the treatment of congenital genetic disease as well as the treatment of cancer or infection.

A method of producing a recombinant viral vector usually comprises introducing elements essential for formation of a virus particle in the form of a nucleic acid construct(s) into a cell to produce a cell having the ability to produce a virus (hereinafter, referred to as a virus-producing cell), and culturing the cell to express the elements essential for formation of the virus particle. In general, of the elements essential for formation of the virus particle, the elements that need to be provided in cis and the elements that can be provided in trans are separately introduced into a cell for viral production, thereby production of a wild-type virus and self-replication of a recombinant virus in a host infected with the virus are prevented (Patent Literature 1).

Hereinafter, as an example, a recombinant AAV vector derived from AAV (hereinafter, referred to as rAAV) is specifically explained. A first established method of producing the viral vector comprises introduction into a host cell of 1) a rAAV plasmid in which an ITR placed at each end of the wild-type AAV genome is left and rep and cap genes are removed and 2) a plasmid for expression of rep and cap genes to provide Rep and Cap proteins in trans, and 3) infection of the host cell with an adenovirus as a helper virus to provide supplemental elements for formation of the infectious virus particle (Patent Literature 2). Use of a herpesvirus or a vaccinia virus as a helper virus instead of an adenovirus has been also known. A vector solution obtained by the above-mentioned method is theoretically contaminated with an adenovirus (or other helper virus). In order to avoid the adenovirus contamination, a method of producing a vector comprising, instead of the above-mentioned 3), 3') introduction of a helper plasmid expressing only elements essential for formation of an AAV virus particle among adenovirus-derived elements (Helper-free system) has been developed (Patent Literature 3).

Virus-producing cells that have accomplished viral production are collected and homogenized to obtain a cell homogenate containing rAAV particles. The cell homogenate is subjected to a suitable step such as filtration with a filter, ultracentrifugation, chromatography, or ultrafiltration to purify the rAAV particles as a final product.

At present, as use of viral vectors is extended to the field of basic research or clinical application for gene therapy, a method of obtaining a virus particle with higher titer and higher purity is needed. Various improved methods are disclosed. For example, a method of enhancing production of virus particles and a release rate of the virus particles into a culture supernatant which comprises culturing a virus-producing cell under a stress condition in which a culture medium has an elevated pH is known (Patent Literature 1). Other methods comprise improvement of steps on and after purification of a produced virus. For purification of virus particles, a quick and simple purification method is proposed (Non-Patent Literature 1). However, the said purification method comprises four steps: two-phase separation of a polyethylene glycol (PEG) phase and an aqueous phase, precipitation with PEG, treatment with chloroform, and dialysis; and thus it is complicated. In addition, a product purified by the purification method contains many bands on SDS-PAGE which are probably derived from impurities. Thus, the purification method is not adequate from the viewpoints of purity and simplicity.

Therefore, there is still room for improvement in treatment of a virus-producing cell performed before purification of virus particles.

CITATION LIST

Patent Literatures

Patent Literature 1: WO00/14205
Patent Literature 2: WO97/06272
Patent Literature 3: WO97/17458

Non-Patent Literatures

Non-Patent Literature 1: J. Virol. Methods, Vol. 183, No. 2, pp. 139-146, 2012

SUMMARY OF INVENTION

Problems to be Solved by the Invention

An objective of the present invention is to provide a method of producing a non-enveloped virus particle with high purity and with no laborious operation.

Solutions to the Problems

The present inventors intently studied for the purpose of providing a method of producing a non-enveloped virus particle with high purity and with no laborious operation, and as a result, found that a non-enveped virus particle with high purity was obtained by treating a sample containing a non-enveloped virus particle with at least two kinds of concentration of PEG. Thus, the present invention was completed.

The present invention generally relates to a method of producing a non-enveloped virus particle, the method comprising:

(a) a step of treating a sample containing a non-enveloped virus particle with a first concentration of polyethylene glycol (PEG), (b) a step of removing a precipitate produced in step (a) and treating a supernatant with a second concentration of PEG, and (c) a step of obtaining a non-enveloped virus particle from a precipitate produced in step (b).

In the method of the present invention, examples of the first concentration of PEG include 0.5 to 4%. Examples of the second concentration of PEG include 3 to 10%. The second concentration of PEG is higher than the first concentration of PEG. In the method of the present invention, the sample containing a non-enveloped virus particle may be a crude extract obtained by bringing a non-enveloped virus-producing cell into contact with an acidic solution, or in the case where a non-enveloped virus particle leaks into a medium during culture of a non-enveloped virus-producing cell, the sample containing a non-enveloped virus particle may be a culture supernatant. In the case where a non-enveloped virus particle is formed in vitro by mixing viral nucleic acid and viral protein in vitro, the mixture may be directly used as the sample. The sample containing a non-enveloped virus particle may be a sample treated with nuclease. The sample containing a non-enveloped virus particle may be a sample treated with chloroform. The sample containing a non-enveloped virus particle may be a crude extract obtained by bringing a non-enveloped virus-producing cell into contact with an acidic solution and then treated with an acid. Further, the method of the present invention may comprise a step of treatment with chloroform after step (c).

In the method of the present invention, the non-enveloped virus may be an adeno-associated virus. In the method of the present invention, the acidic solution may be a solution containing a cation and citric acid.

Effects of the Invention

According to the present invention, a method of producing a non-enveloped virus particle with high purity and with no laborious operation is provided. Further, a non-enveloped virus particle produced by the method is provided. The virus particle produced by the method of the present invention can be applied to a conventional method for purifying a non-enveloped virus.

MODE FOR CARRYING OUT THE INVENTION

The non-enveloped virus as used herein refers to a virus other than an enveloped virus. The enveloped virus refers to a virus having a lipid layer or a lipid bilayer on the viral surface. Representative examples of the non-enveloped virus include DNA genome viruses, for example adenovirus, parvovirus, papovavirus, and human papillomavirus, and RNA genome viruses, for example rotavirus, coxsackie virus, enterovirus, sapovirus, norovirus, poliovirus, echovirus, hepatitis A virus, hepatitis E virus, rhinovirus, and astrovirus.

The non-enveloped virus produced by the production method of the present invention includes, but not limited to, a non-enveloped virus for which a production method has been already known, a non-enveloped virus newly obtained from nature, and gene recombinant viral vectors derived from the above-mentioned non-enveloped viruses. Preferable examples of the non-enveloped virus produced by the production method of the present invention include adenovirus, and AAV belonging to family Parvoviridae.

The "virus particle" as used herein means a particle composed of a protein shell called capsid. The "viral vector" as used herein means a viral genome (the form of nucleic acid) included in the virus particle. For example, in the case of AAV, a rAAV particle is a particle composed of a protein shell called capsid and includes a rAAV vector. The rAAV vector contains a viral genome DNA present in the rAAV particle. The "virus particle" as used herein includes a virus-like particle which does not contain a viral genome (for example, an AAV hollow particle: WO2012/144446). The virus particle includes, but not limited to, a virus-like particle derived from a rAAV vector, and an AAV hollow particle.

The virus-producing cell as used herein refers to a cell expressing elements necessary for viral production and producing virus particles. The virus-producing cell used in the production method of the present invention includes, but not limited to, a virus-producing cell obtained from environment or a clinical sample from a patient with an infection, and an artificially prepared virus-producing cell.

Various cells producing non-enveloped viruses are known, and methods of producing them are also well known. Further, kits for producing recombinant adenovirus vectors or rAAV vector-producing cells are commercially available. Hereinafter, as an example, a rAAV vector is explained. A cell producing a rAAV particle can be produced by introducing elements essential for formation of the rAAV particle, for example, (A) a nucleic acid encoding a Rep protein and a nucleic acid encoding a Cap protein which are derived from AAV, and (B) nucleic acids to provide adenovirus-derived elements, for example, E1a protein, E1b protein, E2 protein, E4 protein, and VA RNA; and (C) a nucleic acid to be enclosed in the rAAV particle, into any cell. A method wherein an adenovirus or the like is used as a helper virus instead of the nucleic acids described in the above (B) is also known.

The "any cell" is not particularly limited. Examples of the "any cell" include cells of mammals such as human, monkey, and rodent, and preferable examples thereof include cells having high transformation efficiency, such as a 293 cell (ATCC CRL-1573), a 293T/17 cell (ATCC CRL-11268), a 293F cell, a 293FT cell (all manufactured by Life Technologies Corp.), a G3T-hi cell (WO06/035829), an AAV293 cell (manufactured by Stratagene Corp.) which is a commercially available cell line for viral production, and insect cells such as an Sf9 cell (ATCC CRL-1711). For example, the 293 cell or the like constantly expresses adenovirus E1 protein. Also, a cell modified to transiently or constantly express one or some of proteins necessary for rAAV production may be used.

The nucleic acid encoding a Rep protein and the nucleic acid encoding a Cap protein which are derived from AAV, and the nucleic acids to provide adenovirus-derived elements may be in any form which is not limited. These nucleic acids can be inserted into a plasmid or a viral vector as one or more nucleic acid constructs capable of providing the elements, and then the plasmid or the viral vector can be introduced into a cell. The introduction of these nucleic acids into a cell can be performed by a known method using a commercially available or known plasmid or viral vector.

The nucleic acid to be enclosed in the rAAV particle is composed of ITR sequences derived from AAV and a nucleic acid desired to be carried by a rAAV vector. Examples of the nucleic acid desired to be carried by a rAAV vector include any foreign gene, for example a nucleic acid for providing a polypeptide (enzyme, growth factor, cytokine, receptor, structural protein, etc.), an antisense RNA, a ribozyme, a decoy, an RNA that induces RNA interference, or the like. In addition, for control of expression of the foreign gene, a suitable promoter, enhancer, terminator and other transcriptional regulatory elements may be inserted into the nucleic acid. For example, the nucleic acid to be enclosed in the rAAV particle may contain any foreign gene desired to be carried by the rAAV vector between two ITR sequences, or may contain any foreign gene desired to be carried by the rAAV vector and at least one element for control of expression of the foreign gene between two ITR sequences. The nucleic acid to be enclosed in the virus particle can be introduced as a nucleic acid construct in the form of a plasmid into a cell. The plasmid can be constructed, for example, by use of a pAAV-CMV vector (manufactured by TAKARA BIO Inc.) which is commercially available, or the like. The nucleic acid to be enclosed in the virus particle can be also introduced into a cell by infection with a viral vector retaining a genome containing the nucleic acid sequence. As the viral vector, for example, but not limited to, a baculovirus vector can be used.

Culture of the non-enveloped virus-producing cell can be performed under known culture conditions. When the non-enveloped virus-producing cell is derived from a mammal cell, for example, the cell is cultured at a temperature of 30 to 37° C., a humidity of 95%, and a $CO_2$ concentration of 5 to 10%. When the non-enveloped virus-producing cell is derived from an insect cell, for example, the cell is cultured at a temperature of 26 to 30° C. under shaking. However, culture conditions of the non-enveloped virus-producing cell are not limited to the above-described culture conditions. The cell culture may be performed at a temperature, a humidity and a $CO_2$ concentration out of the above-described ranges, as long as desired cell growth and production of the non-enveloped virus are accomplished. A culture period is not particularly limited, and may be any period as long as desired cell growth and production of the non-enveloped virus are accomplished. When the non-enveloped virus-producing cell is derived from a mammal cell, for example, the cell culture is continued for 12 to 150 hours, preferably 48 to 120 hours, after introduction of the elements essential for formation of the non-enveloped virus particle into the cell. When the non-enveloped virus-producing cell is derived from an insect cell, for example, the cell culture is continued for 3 to 11 days, preferably 5 to 9 days, after introduction of the elements essential for formation of the non-enveloped virus particle into the cell.

The sample containing a non-enveloped virus particle used in the present invention can be prepared by, but not limited to, destruction or dissolution of the non-enveloped virus-producing cell cultured as described above. In the case where non-enveloped virus particles leak into a medium during culture of the non-enveloped virus-producing cell, a culture supernatant can be also used as the sample in the present invention. In the case where non-enveloped virus particles are formed in vitro by mixing viral nucleic acid and viral protein in vitro, the mixture can be also used as the sample in the present invention. The destruction or dissolution of the non-enveloped virus-producing cell can be performed by a known method such as ultrasonic treatment, freeze-thaw treatment, enzymatic treatment, or osmotic pressure treatment. Further, as described in Examples later, the sample containing a non-enveloped virus can be also obtained by bringing the non-enveloped virus-producing cell into contact with an acidic solution. This step is performed by suspending a pellet of the non-enveloped virus-producing cell in an acidic solution, wherein the pellet is collected by removing a culture solution by centrifugation or filtration after the cell culture, or by adding a component to the culture solution of the non-enveloped virus-producing cell, wherein the component is a component capable of making the culture solution acidic. Examples of temperature and time for the contact with the acidic solution include, but not particularly limited to, 0 to 40° C., preferably 4 to 37° C., and 1 minute to 48 hours, preferably 5 minutes to 24 hours. This contact step results in the release of non-enveloped virus particles outside the producing cell. The non-enveloped virus particle is used, in a state of contact with the acidic solution or in a state after neutralization, as the sample containing a non-enveloped virus particle in the method of the present invention. The non-enveloped virus particle can be stored in a state of contact with the acidic solution or in a state after neutralization in an ultra-deep freezer, for example at −80° C., for a long time.

The acidic solution refers to a solution showing acidity. The acidic solution is not limited, as long as the acidic solution shows a lower oH than of the non-enveloped virus-producing cell being cultured and the sample containing a non-enveloped virus particle is obtained by treating the non-enveloped virus-producing cell that has accomplished the viral production with the acidic solution. The acidic solution used in the present invention has, for example, a pH of 3.0 to 6.9, preferably a pH of 3.0 to 6.0, more preferably a pH of 3.0 to 5.0. Examples of the acidic solution used in the present invention include solutions containing a compound selected from the group consisting of citric acid, acetic acid, malic acid, phosphoric acid, hydrochloric acid, sulfuric acid, nitric acid, lactic acid, propionic acid, butyric acid, oxalic acid, malonic acid, succinic acid, fumaric acid, maleic acid, tartaric acid, benzoic acid, sulfosalicylic acid, formic acid, and their salts, and Good's buffers having a buffering region at pH 7 or lower such as MES, and Bis-Tris. In the present invention, an acidic solution containing citric acid, acetic acid, phosphoric acid, or a salt thereof is preferably used. The concentration of the compound contained in the acidic solution is preferably 5 mM to 1 M, more preferably 10 to 500 mM.

A solvent for preparing the acidic solution is not particularly limited. The solvent can be appropriately selected from water, buffers, media for cell culture, and the like. The solvent may contain various ions depending on the subsequent operation. Examples of such ions include, but not limited to, cations such as a sodium ion, potassium ion, and a magnesium ion. Preferable examples of the solvent for the acidic solution used in the present invention include water, an aqueous solution containing a cation such as a sodium ion, a potassium ion and/or a magnesium ion, such as a sodium chloride solution, a potassium chloride solution, a magnesium chloride solution and a physiological saline, and a solution containing a saccharide such as a glucose solution and a sucrose solution. The sodium ion concentration and/or the potassium ion concentration in the acidic solution is not particularly limited, and it is for example 5 mM to 2.7 M, preferably 5 mM to 1 M, more preferably 20 to 800 mM. For example, though a 30 to 40 mM citrate buffer solution contains about 200 mM sodium ion, an acidic solution prepared by adding further 50 to 100 mM sodium ion to the citrate buffer solution may be used.

The component capable of making the culture solution of the non-enveloped virus-producing cell acidic when added to the culture solution is not limited, as long as the component changes the pH of the culture solution into lower pH than that of the non-enveloped virus-producing cell being cultured and the component allows for preparation of a crude extract containing non-enveloped virus particles from the non-enveloped virus-producing cell that has accomplished the viral production. Examples of the component capable of making the culture solution acidic used in the present invention include citric acid, acetic acid, malic acid, phosphoric acid, hydrochloric acid, sulfuric acid, nitric acid, lactic acid, propionic acid, butyric acid, oxalic acid, malonic acid, succinic acid, fumaric acid, maleic acid, tartaric acid, benzoic acid, sulfosalicylic acid, formic acid, and their salts, and the same solutions as the above-described acidic solutions. The addition amount of the component capable of making the culture solution acidic is not particularly limited as long as a crude extract containing non-enveloped virus particles is obtained from the non-enveloped virus-producing cell that has accomplished the viral production, and may be appropriately determined by a person skilled in the art. In addition, various ionic components may be added together with the component capable of making the culture solution acidic. For example, the same ionic solutions as described above for the acidic solution may be used as the ionic components.

In the method of the present invention, the sample containing a non-enveloped virus particle (hereinafter, also referred to as "the crude extract of virus particle") as obtained through the above-described steps is treated with the concentration of polyethylene glycol (PEG) at which the non-enveloped virus particle is less likely to precipitate, that is, a first concentration of PEG. In the presence of the first concentration of PEG, a part of impurities selectively precipitate. Examples of the first PEG concentration include a range of 0.5 to 4% (hereinafter % means W/V), preferably a range of 1 to 3%. It should be appreciated that the suitable PEG concentration may be appropriately determined by, for example, a method described in Example 1.

In the present invention, precipitates produced by the treatment with the first concentration of PEG are removed to obtain a supernatant, and then the supernatant is treated with a second concentration of PEG. The second concentration is higher than the first concentration. In the presence of the second concentration of PEG, the non-enveloped virus particle precipitates, and thus the non-enveloped virus particle is separated from soluble impurities. Examples of the second PEG concentration include a range of 3 to 10%, preferably a range of 4 to 8%. It should be appreciated that the suitable PEG concentration may be appropriately determined by, for example, a method described in Example 1. The non-enveloped virus particle precipitated by the treatment with the second concentration of PEG is collected by a known method such as filtration or centrifugation. Since in the method of the present invention, purification and concentration can be performed at the same time, a sample containing non-enveloped virus particles at a low concentration can be preferably used in the method of present invention. For example, but not limited to, the method of the present invention is used to collect non-enveloped virus particles that have leaked into a culture supernatant.

The PEG used in the method of the present invention is not particularly limited, and PEG having various average molecular weights can be used. For example, PEG having an average molecular weight of 200 to 10,000, preferably an average molecular weight of 4,000 to 10,000 is used in the present invention. More preferably, PEG having an average molecular weight of 6,000 to 8,000 can be used. The treatment of a sample containing a non-enveloped virus particle with the first concentration of PEG, and the treatment of a supernatant obtained by the treatment with the first concentration of PEG with the second concentration of PEG are preferably performed by adding a previously prepared PEG solution to the sample or the supernatant so that the final concentration in the sample or the supernatant becomes the first concentration or the second concentration, though they may be also performed by adding solid PEG to the sample or the supernatant. The treatment with the first concentration of PEG and the treatment with the second concentration of PEG are performed by adding PEG to the sample and the supernatant so as to become the predetermined concentration of PEG, and then leaving the sample and the supernatant to stand at low temperature, for example at 0 to 10° C., for example for 1 minute to 48 hours, preferably for 5 minutes to 24 hours, more preferably 30 minutes to 2 hours. these PEG treatments, a supernatant and precipitates may be separated by a known method such as filtration, preferably centrifugation.

The method of producing a non-enveloped virus of the present invention can be combined with a known method of purifying a virus. For example, before the treatment with the first concentration of PEG, the sample containing a non-enveloped virus particle (the crude extract of virus particle) may be treated with nuclease. The nuclease used in this step is preferably a nuclease that acts on DNA contained in the crude extract. Examples of the nuclease include BENZONASE (registered trademark) (manufactured by Merck Millipore Corporation), and Cryonase Cold-active nuclease (manufactured by TAKARA BIO INC.). Temperature and time for the nuclease treatment step is not particularly limited, and may be appropriately determined depending on the kind of nuclease to be used. Before the treatment with the first concentration of PEG, the sample containing a non-enveloped virus particle (the crude extract of virus particle) may be also treated with an acid to precipitate impurities. The acid is not particularly limited as long as it lowers the pH of the sample containing a non-enveloped virus particle. Examples of the acid include the same acidic solutions and acidic components as those cited as examples of the acidic solution or the component capable of making the culture solution acidic used for preparation of the sample containing a non-enveloped virus particle. In the case where the sample containing a non-enveloped virus particle is a crude extract obtained by bringing a non-enveloped virus-producing cell into contact with an acidic solution, the acidic solution or the acidic component that is used for preparation of the sample containing a non-enveloped virus particle may be the same kind of acid as or a different kind of acid from the acidic solution or the acidic component that is used for the acid treatment of the sample containing a non-enveloped virus particle before the treatment with the first concentration of PEG. Temperature and time for the acid treatment step is not particularly limited, and may be appropriately determined. Examples of temperature and time for the acid treatment step include 0 to 10° C., and 1 minute to 48 hours, preferably 5 minutes to hours, more preferably 30 minutes to 2 hours. For example, when the crude extract is obtained by treating the cell with a 30-40 mM citrate buffer solution, citric acid or a citrate buffer is added to the crude extract so that the final concentration of citric acid is increased by 50-200 mM, thereby impurities contained in the crude extract can be precipitated. "The sample containing a non-enveloped virus particle (the crude extract of virus particle)" obtained after the acid treatment is used in the next step, in a state of acidic or after neutralization.

The method of the present invention can be also combined with a chloroform treatment. For example, the sample containing a non-enveloped virus particle may be previously treated with chloroform and then treated with the first concentration of PEG and the second concentration of PEG, or the sample containing a non-enveloped virus particle may be treated with chloroform after completion of the tow-stage PEG treatment. These chloroform treatments may be performed in combination. The chloroform treatment step may be performed according to a conventional method. An example of the chloroform treatment comprises addition of chloroform (99% purity) to a solution containing a non-enveloped virus particle in the same volume as that of the solution, sufficient stirring, and then centrifugation. In a supernatant (aqueous phase) thus obtained, the non-enveloped virus particle is present, impurities are present in a chloroform phase or an interface.

The method of the present invention may be combined with any one or two or more treatments selected from the group consisting of the nuclease treatment, the acid treatment and the chloroform treatment of the sample containing a non-enveloped virus particle before the treatment with the first concentration of PEG, and the chloroform treatment after the treatment with the second concentration of PEG. When the method of the present invention is combined with two or more treatments of the nuclease treatment, the acid treatment and the chloroform treatment of the sample containing a non-enveloped virus particle before the treatment with the first concentration of PEG, these treatments may be performed in any order.

The non-enveloped virus particle obtained as a partially purified product via the two-stage PEG treatment as described above can be subsequently subjected to purification by ultracentrifugation, chromatography, ultrafiltration, or another known method to obtain a concentrated or purified non-enveloped virus particle as a final product. The purification of the non-enveloped virus particle by chromatography can be performed by an ion-exchange column (for example, Mustang Q manufactured by Pall Corp.), an affinity column (for example, AVE Sepharose manufactured by GE Healthcare Ltd., or a heparin column), a hydroxyapatite column, or the like. The purification of the non-enveloped virus particle can be also performed by the treatment with high concentration of acid as described above to precipitate impurities.

As used herein, the yield of the non-enveloped virus particle is shown as a titer of the non-enveloped virus or the like. The titer of the non-enveloped virus is shown as, but not limited to, in a certain amount of a sample, a) the number of genomes (genomic titer) of the non-enveloped virus, b) the infection ability (infectious titer) of the non-enveloped virus to a cell as determined experimentally, or c) the purity of protein constituting the non-enveloped virus as measured, and the type of titer is specified as necessary.

Examples of a method for determination of the genomic titer include a method comprising determination of the copy number of the virus genome in a sample by PCR.

Examples of a method for determination of the infectious titer include a method comprising infection of a suitable target cell with serially diluted solutions of the non-enveloped virus, and detection of change in the form of the cell (cytopathy), a method comprising detection of the expression of a transgene, and a method comprising determination of the copy number of the virus genome introduced into the cell.

Examples of a method for determination of the purity of protein constituting the non-enveloped virus include a method comprising SDS-PAGE analysis of the protein and a method comprising quantitative determination of the protein by an immunological technique.

Further, an aspect of the present invention provides a kit for producing a non-enveloped virus particle. The kit contains PEG suited for the treatments of the sample containing a non-enveloped virus particle with the first concentration of PEG and the second concentration of PEG in the method of producing a non-enveloped virus particle of the present invention, for example, PEG solutions that give the above-described two kinds of concentration when they are added to the sample. The kit may further contain a reagent to be used for preparation of the crude extract from the non-enveloped virus-producing cell, for example, an acidic solution, a vector comprising a nucleic acid to provide elements essential for particle formation of a non-enveloped virus, a vector comprising a nucleic acid to be enclosed in the particle of the non-enveloped virus, and the like.

According to the present invention, in addition to the method of producing a non-enveloped virus particle, the kit for use in the production method, and the non-enveloped virus particle produced by the production method are provided. In addition, a pharmaceutical composition comprising the non-enveloped virus particle produced by the production method of the present invention as an active ingredient is provided. The pharmaceutical composition can be appropriately prepared according to techniques for production of viral formulations for gene therapy. For example, the non-enveloped virus particle obtained by the production method of the present invention can be further concentrated, purified and processed by known methods, and then formulated into a pharmaceutical composition. The pharmaceutical composition can be used ex vivo for cells from patients, or administered directly to patients.

EXAMPLES

Hereinafter, the present invention is more specifically explained by way of Examples which the present invention is not limited to.

Example 1

Investigation of PEG Concentration for Precipitation (1) Seeding of Cell for Production of rAAV Particle In DMEM (manufactured by Sigma-Aldrich Co. LLC.) containing 10% FBS (manufactured by Hyclone Laboratories), 293T/17 cells were suspended. The suspension was seeded in a CellBIND (registered trademark) T225 flask (manufactured by Corning Inc.), and then, cultured in a $CO_2$ incubator at 37° C. for 3 days. The cells were confirmed to be about 70% confluent.

(2) Transfection of Plasmid for Production of rAAV Particle

The cells obtained by Example 1-(1) were transfected with each 25 µg of a pRC plasmid containing sequences encoding the Rep protein and the Cap protein of AAV type 2 (hereinafter, referred to as AAV2) (manufactured by Cell Biolabs, Inc.), a pHLP plasmid containing sequences encoding adenovirus-derived E2A, VA and V4 (manufactured by Cell Biolabs, Inc.), and a pAAV-AsRed2 plasmid containing "a CMV promoter sequence, a sequence encoding AsRed2, and a PolyA sequence" as an expression cassette for fluorescent protein AsRed2 between two ITRs of AAV2 genome (for example, a plasmid described in WO2014/007120) by using the calcium phosphate method. Six hours after the transfection, the medium was completely removed, and 40 mL/flask of DMEM containing 2% fetal bovine serum (FBS) was added to the flask. The cells were cultured in a $CO_2$ incubator at 37° C. for 2 days.

(3) Preparation of Crude Extract by Citrate Buffer Treatment

To the flask obtained by Example 1-(2), 0.5 mL of 0.5 M EDTA (manufactured by Wako Pure Chemical Industries, Ltd.) was added, followed by incubation at room temperature for several minutes to dissociate the cells. Then, the culture solution containing the cells was collected, centrifuged at 1,750×g, at 4° C., for 10 minutes. Then, a supernatant was removed. A cell pellet was resuspend in 2 mL of 38.1 mM citrate buffer (38.1 mM citric acid, 74.8 mM sodium citrate, 75 mM sodium chloride), mixed for 15 seconds by a vortex mixer, left standing in a water bath at 37° C. for 5 minutes, again mixed by a vortex mixer for 15 seconds, and then centrifuged at 14,000×g, at 4° C., for 10 minutes to collect a supernatant. To the supernatant, 1/10 volume of 2 M Tris-HCl (pH 9.5) was added, and the solution thus obtained was used as a crude extract.

(4) PEG Precipitation

To the crude extract obtained by Example 1-(3), 1/100 volume of 1 M $MgCl_2$ was added, followed by treatment with BENZONASE (manufactured by Merck Millipore Corporation) (final concentration: 250 U/mL) at 37° C. for 1 hour. After the BENZONASE treatment, a 60% solution of polyethylene glycol (PEG)-8000 (manufactured by Promega Corporation) was added to the crude extract so that the final concentration of PEG became 8%, 6%, 4%, 2%, or 1%, mixed, and left standing on ice for 30 minutes. Then, the mixture was centrifuged at 1,500×g, at 4° C., for 30 minutes. A supernatant was removed and a pellet was collected. The pellet was suspended in a solution containing 25 mM EDTA, 150 mM NaCl, and 50 mM HEPES (pH 7.4), and left standing overnight at 4° C. to obtain a PEG precipitation solution.

(5) Determination of Genomic Titer

Two microliters of the crude extract obtained by Example 1-(3) or the PEG precipitation solution obtained by Example 1-(4) was added to 18 µl of a reaction solution of DNaseI (manufactured by TAKARA BIO Inc.) that was prepared according to the instructions, mixed, and then subjected to enzymatic reaction to remove free genomic DNA and plasmid DNA. Then, heat treatment at 99° C. for 10 minutes for inactivation of DNaseI was performed to obtain a DNaseI-treated rAAV particle-containing solution. To 20 µl of the DNaseI-treated rAAV particle-containing solution, 15 µL of water for injection (manufactured by Otsuka Pharmaceutical Co., Ltd.), 4 µL of 10× Proteinase K buffer [0.1 M Tris-HCl (pH 7.8), 0.1 M EDTA, 5% SDS], and 1 µL of Proteinase K (manufactured by TAKARA BIO Inc.) were added, and maintained at 55° C. for 1 hour. The reaction solution was subjected to heat treatment at 95° C. for 10 minutes for inactivation of Proteinase K, and then stored at 4° C. 20° C. The solution was 50-fold diluted with water for injection, and 2 µl of the dilution was used for determination of the genomic titer of the rAAV vector particle. For determination of genomic titer, SYBR Premix ExTaqII (manufactured by TAKARA BIO Inc.) was used, and operations including preparation of a reaction solution etc. followed the instructions attached to the kit. As standard, a linearized DNA obtained by digestion of a pAAV-AsRed2 plasmid with restriction enzyme BglIII (manufactured by TAKARA BIO Inc.) was used. Primer sequences used in realtime PCR are sequences that anneal to the CMV promoter sequence placed in the AsRed2 expression cassette. Results are shown in Table 1.

TABLE 1

| Sample | Total genomic titer (×10^10 VG) |
|---|---|
| Crude extract | 4.82 |
| 8% PEG precipitation | 4.58 |
| 6% PEG precipitation | 4.94 |
| 4% PEG precipitation | 4.01 |
| 2% PEGprecipitation | 1.37 |
| 1% PEG precipitation | 0.23 |

VG = Vector genome

As seen from Table 1, the crude extract, 8% PEG precipitation, 6% PEG precipitation, and 4% PEG precipitation had almost equal genomic titer. In contrast, 2% PEG precipitation and 1% PEG precipitation had remarkably low genomic titer as compared with the other samples. These results show that a rAAV vector is less likely to precipitate by treatment with 2% PEG or 1% PEG.

(6) Determination of Protein Purity

Figure 1:
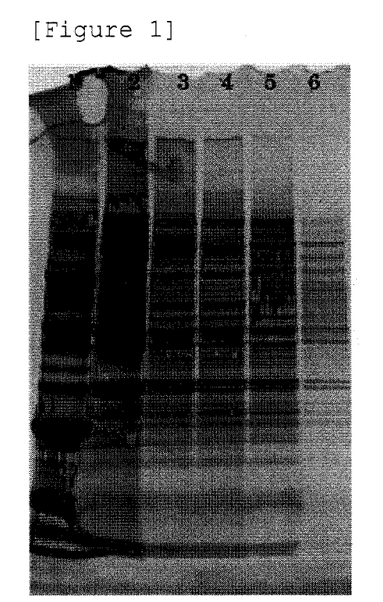
FIG. 1 An SDS-PAGE photograph of samples treated with each PEG concentration.

To 10 µL of the crude extract obtained by Example 1-(3) or the PEG precipitation solution obtained by Example 1-(4), 10 µL of 2× sample buffer (manufactured by TAKARA BIO Inc.) was added, and mixed at 95° C. for 10 minutes. Each sample (10 µL) was applied onto 4-20% acrylamide gel (manufactured by ATTO Corp.) and electrophoresed. After completion of electrophoresis, the gel was immersed in a suitable amount of an Oriole fluorescent gel stain solution (manufactured by Bio-Rad Laboratories, Inc.), and shaken under light shielding for 90 minutes. After shaking, the gel was photographed with Luminoshot 400 (manufactured by TAKARA BIO Inc.). Results are shown in FIG. 1. In FIG. 1, each lane is as follows: lane 1: crude extract, lane 2: 8% PEG precipitation, lane 3: 6% PEG precipitation, lane 4: 4% PEG precipitation, lane 5: 2% PEG precipitation, lane 6: 1% PEG precipitation.

As seen from FIG. 1, 6% PEG precipitation, 4% PEG precipitation, and 2% PEG precipitation had almost the same electrophoresis pattern. These results show that almost the same impurities precipitate under the conditions of 6% PEG precipitation, 4% PEG precipitation, and 2% PEG precipitation. Considering the results of Table 1 showing that a rAAV particle is less likely to precipitate by treatment with 2% PEG, it was found that only impurities can be precipitated and removed with less precipitation of a rAAV particle in the presence of about 2% concentration of PEG.

Example 2

Removal of Impurity by PEG Precipitation Operation (1) Preparation of Crude Extract by Citrate Buffer Treatment A crude extract was prepared in the same manner as Example 1-(1) to (3). To the crude extract, 1/100 volume of 1 M $MgCl_2$ was added, followed by treatment with BENZONASE at 37° C. for 1 hour.

(2) PEG Precipitation, Washing, and Concentration by 100K UF

The BENZONASE-treated crude extract obtained by Example 2-(1) was subjected to any one of the following treatment A to F to prepare a sample.

A: To the BENZONASE-treated crude extract, a 60% PEG-8000 solution was added so that the final concentration of PEG became 8%, mixed, and left standing on ice for 30 minutes. Then, the mixture was centrifuged at 1,500×g, at 4° C., for 30 minutes to collect a pellet. The pellet was suspended in PBS (manufactured by Gibco), and left standing overnight at 4° C. to dissolve the pellet. Thus sample A was prepared.

B: A pellet was obtained in the same manner as A. The pellet was rinsed with an 8% PEG-8000 solution, and then suspended in PBS (manufactured by Gibco). The suspension was left standing overnight at 4° C. to dissolve the pellet. Thus sample B was prepared.

C: The same as sample B was prepared in the same manner as B, and then concentrated by 100K ultrafiltration centrifugal unit (100K UF) (manufactured by Merck Millipore Corp.). Thus sample C was prepared.

D: To the BENZONASE-treated crude extract, a 60% PEG-8000 solution was added so that the final concentration of PEG became 2%, mixed, and left standing on ice for 30 minutes. Then, the mixture was centrifuged at 1,500×g, at 4° C., for 30 minutes to collect a supernatant. To the supernatant, a 60% PEG-8000 solution was added so that the final concentration of PEG became 8%, mixed, and left standing on ice for 30 minutes. Then, the mixture was centrifuged at 1,500×g, at 4° C., for 30 minutes to collect a pellet. The pellet was suspended in PBS (manufactured by Gibco), and left standing overnight at 4° C. to dissolve the pellet. Thus sample D was prepared.

E: A pellet was obtained in the same manner as D. The pellet was rinsed with an 8% PEG-8000 solution, and then suspended in PBS (manufactured by Gibco). The suspension was left standing overnight at 4° C. to dissolve the pellet. Thus sample E was prepared.

F: The same as sample E was prepared in the same manner as E, and then concentrated by 100K ultrafiltration centrifugal unit (100K UF) (manufactured by Merck Millipore Corp.). Thus sample F was prepared.

(3) Determination of Genomic Titer

The total genomic titer of sample A to F obtained by Example 2-(2) was determined in the same manner as Example 1-(5). Results are shown in Table 2.

TABLE 2

| Sample | Total genomic titer (×10^10 VG) |
| --- | --- |
| BENZONASE-treated crude extract | 4.46 |
| A: 8% PEG precipitation | 4.48 |
| B: 8% PEG precipitation, 8% PEG washing | 3.93 |
| C: 8% PEG precipitation, 8% PEG washing, 100K UF | 2.67 |
| D: 2-8% PEG precipitation | 2.00 |
| E: 2-8% PEG precipitation, 8% PEG washing | 2.09 |
| F: 2-8% PEG precipitation, 8% PEG washing, 100K UF | 1.35 |

As seen from Table 2, the total genomic titer of the samples (D, E) that were subjected to removal of precipitates by 2% PEG precipitation was about half the total genomic titer of the samples (A, B) that were not subjected to removal of precipitates by 2% PEG precipitation. These results show that after removal of precipitates by 2% PEG precipitation, a recovery rate of the sample is about 50%.

(4) Determination of Protein Purity

Figure 2:
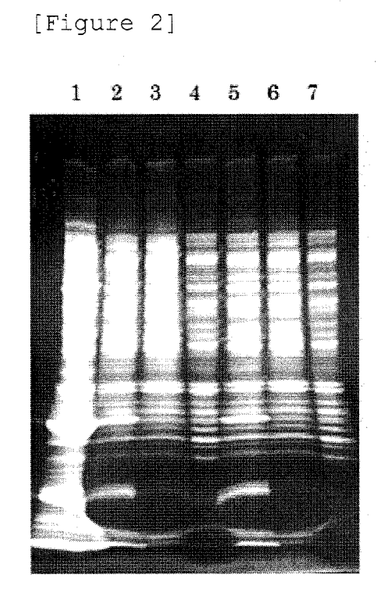
FIG. 2 An SDS-PAGE photograph of samples treated with two-staged PEG concentration.

The purity of the samples obtained by Example 2-(2) was determined in the same manner as Example 1-(6). Results are shown in FIG. 2. In FIG. 2, lane 1 to lane 7 show the results in the order of BENZONASE-treated crude extract, and sample A to sample F.

As seen from FIG. 2, the samples (D, E) that were subjected to removal of precipitates by 2% PEG precipitation had a smaller number of bands than the samples (A, B) that were not subjected to removal of precipitates by 2% PEG precipitation. These results show that use of a supernatant obtained after the 2% PEG precipitation operation makes it possible to produce a rAAV particle with higher purity than simple 8% PEG precipitation.

Example 3

Removal of Impurity by Combination of PEG Precipitation Operation and Chloroform Treatment (1) Preparation of Crude Extract by Citrate Buffer Treatment A crude extract was prepared in the same manner as Example 1-(1) to (3). To the crude extract, 1/100 volume of 1 M $MgCl_2$ was added, followed by treatment with BENZONASE at 37° C. for 1 hour.

(2) PEG Precipitation, and Chloroform Treatment

The BENZONASE-treated crude extract obtained by Example 3-(1) was subjected to any one of the following treatment G to J to prepare a sample.

G: To the BENZONASE-treated crude extract, an equal amount of chloroform (99% purity) was added, mixed by a vortex mixer for 10 seconds, and then centrifuged at 14,000×g, at 4° C., for 10 minutes to collect a supernatant (these operations are referred to as "the chloroform treatment"). To the supernatant, a 60% PEG-8000 solution was added so that the final concentration of PEG became 1%, mixed, and left standing on ice for 30 minutes. Then, the mixture was centrifuged at 1,500×g, at 4° C., for 30 minutes to collect a supernatant. To the supernatant, a 60% PEG-8000 solution was added so that the final concentration of PEG became 5%, mixed, and left standing on ice for 30 minutes. Then, the mixture was centrifuged at 1,500×g, at 4° C., for 30 minutes to collect a pellet. The pellet was suspended in PBS (manufactured by Gibco), and left standing overnight at 4° C. to dissolve the pellet. Thus sample G was prepared.

H: The same as sample G was prepared in the same manner as G, and then subjected to the chloroform treatment to obtain a supernatant. Thus sample H was prepared.

I: To the BENZONASE-treated crude extract, a 60% PEG-8000 solution was added so that the final concentration of PEG became 1%, mixed, and left standing on ice for 30 minutes. Then, the mixture was centrifuged at 1,500×g, at 4° C., for 30 minutes to collect a supernatant. To the supernatant, a 60% PEG-8000 solution was added so that the final concentration of PEG became 5%, mixed, and left standing on ice for 30 minutes. Then, the mixture was centrifuged at 1,500×g, at 4° C., for 30 minutes to collect a pellet. The pellet was suspended in PBS (manufactured by Gibco), and left standing overnight at 4° C. to dissolve the pellet. Thus sample I was prepared.

J: The same as sample I was prepared in the same manner as I, and then subjected to the chloroform treatment to obtain a supernatant. Thus sample J was prepared.

(3) Determination of Genomic Titer

The total genomic titer of the samples obtained by Example 3-(2) was determined in the same manner as Example 1-(5). Results are shown in Table 3.

TABLE 3

| Sample | Total genomic titer ($\times 10^{10}$ VG) |
|---|---|
| Crude extract | 11.2 |
| G: Chloroform treatment, 1-5% PEG precipitation | 6.27 |
| H: Chloroform treatment, 1-5% PEG precipitation, Chloroform treatment | 5.73 |
| I: 1-5% PEG precipitation | 7.60 |
| J: 1-5% PEG precipitation, Chloroform treatment | 6.10 |

As seen from Table 3, the total genomic titer of the samples that were subjected to the chloroform treatment was almost equal to the total genomic titer of the samples that were not subjected to the chloroform treatment. These results show that when the PEG precipitation and the chloroform treatment are combined, the titer of a rAAV particle is not impaired by the chloroform treatment.

(4) Determination of Protein Purity

Figure 3:
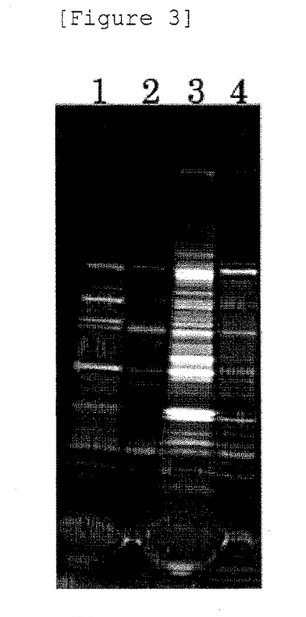
FIG. 3 An SDS-PAGE photograph of samples treated with two-staged PEG concentration, and chloroform.

The purity of the samples obtained by Example 3-(2) was determined in the same manner as Example 1-(6). Results are shown in FIG. 3. In FIG. 3, each lane is as follows: lane 1: G, lane 2: H, lane 3: I, lane 4: J.

As seen from FIG. 3, the samples that were subjected to the chloroform treatment had a smaller number of bands than the samples that were not subjected to the chloroform treatment. These results show that when the PEG precipitation and the chloroform treatment are combined, impurities are removed by the chloroform treatment. Considering the results shown by Table 3, it was found that a rAAV particle with high titer and high purity can be produced by the combination of the PEG precipitation and the chloroform treatment.

Example 4

Removal of Impurity by Addition of Citric Acid and PEG Precipitation Operation (1) Preparation of Crude Extract by Citrate Buffer Treatment A crude extract was prepared in the same manner as Example 1-(1) to (3).

(2) Citric Acid Precipitation

To the crude extract obtained by Example 4-(1), 1/20 volume of a 2 M citric acid solution was added, mixed well, and left standing at 4° C. for 90 minutes. Then, the mixture was centrifuged at 2,380×g, at 4° C., for 20 minutes to collect a supernatant as a citric acid-treated supernatant.

(3) PEG Precipitation

To the citric acid-treated supernatant obtained by Example 4-(2), 1/4 volume of a 2 M Tris-HCl solution (pH 9.0) and 1/100 volume of 1 M $MgCl_2$ were added, followed by treatment with BENZONASE at 37° C. for 1 hour according to the instructions attached thereto. Then, a 40% solution of PEG-6,000 (manufactured by nacalai tesque) was added to the mixture so that the final concentration of PEG became 1%, mixed, and left standing on ice for 30 minutes. Then, the mixture was centrifuged at 2,380×g, at 4° C., for 30 minutes to collect a supernatant. To the supernatant, a 40% PEG-6,000 solution was added so that the final concentration of PEG became 8%, mixed, and left standing on ice for 60 minutes. Then, the mixture was centrifuged at 2,380×g, at 4° C., for 30 minutes to collect a pellet. The pellet was suspended in a solution containing 10 mM $MgCl_2$, 75 mM NaCl, and 50 mM HEPES (pH 8.0), and left standing overnight at 4° C. Then, the suspension was centrifuged at 2,380×g, at 4° C., for 10 minutes to collect supernatant 1. The remaining pellet was resuspended in HNE buffer (50 mM HEPES, 150 mM NaCl, 25 mM EDTA), immediately centrifuged at 2,380×g, at 4° C., for 10 minutes to collect supernatant 2.

(4) Determination of Genomic Titer

The genomic titer of the samples obtained by Example 4-(2) and Example 4-(3) was determined in the same manner as Example 1-(5). Results are shown in Table 4.

TABLE 4

| Sample | Total genomic titer ($\times 10^{10}$ VG) |
|---|---|
| Before PEG precipitation (Citric acid-treated supernatant) | 12.2 |
| After 8% PEG precipitation (Supernatant 1 + Supernatant 2) | 9.26 |

As seen from Table 4, the genomic titer after the PEG precipitation operation was not much changed from the genomic titer before the PEG precipitation operation.

(5) Determination of Protein Purity

Figure 4:
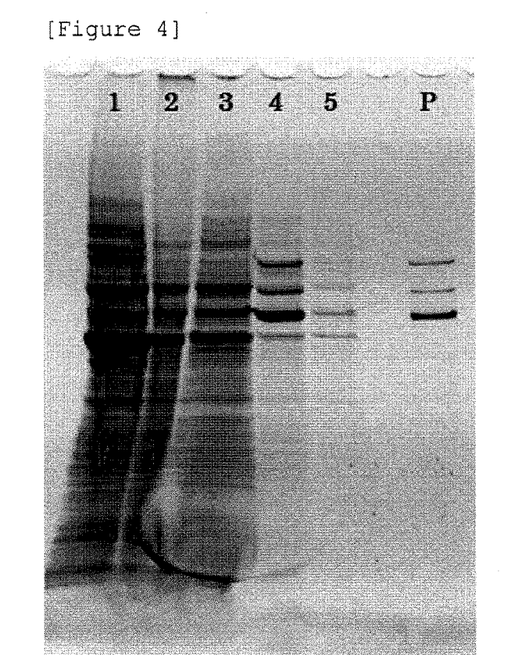
FIG. 4 An SDS-PAGE photograph of samples treated with high concentration of acid, and two-staged PEG concentration.

The purity of the samples obtained by Example 4-(2) and Example 4-(3) was determined in the same manner as Example 1-(6). As a comparative control, a rAAV particle purified by ultracentrifugation was used. Results are shown in FIG. 4. In FIG. 4, each lane is as follows: lane 1: crude extract, lane 2: citric acid-treated supernatant, lane 3: supernatant after 1% PEG precipitation, lane 4: 8% PEG precipitation (supernatant 1), lane 5: 8% PEG precipitation (supernatant 2), lane P: ultracentrifugation-purified rAAV particle (comparative control).

As seen from FIG. 4, supernatant 1 had a smaller number of bands than the crude extract and the citric acid-precipitation solution. Considering the results shown by Table 4, it was found that a rAAV particle with high titer and high purity can be produced by the combination of the citric acid precipitation and the PEG precipitation.

Example 5

Removal of Impurity from Insect Cell Culture Supernatant by Two-stage PEG Precipitation Operation (1) Culture of Insect Cell for Production of rAAV Particle In CELLBAG (registered trademark) (manufactured by GE Healthcare), 2 L of a suspension of Sf9 cells in PSFM-J1 medium (manufactured by Wako Pure Chemical Industries, Ltd.) was seeded. Then, the cells were cultured at 28° C. under shaking until the cell density reached about $2\times10^6$ cells/mL.

(2) Infection with Baculovirus Vector for Production of rAAV Particle

The cells obtained by Example 5-(1) were coinfected with "a baculovirus vector retaining a genome containing a vector genome sequence containing an expression cassette for a gene of interest between two ITR regions of AAV2 genome" and "a baculovirus vector retaining a genome containing sequences encoding the Rep protein of AAV2 and the Cap protein of AAV8" at MOI=0.3, and cultured for 7 days.

(3) Preparation of Insect Cell Culture Supernatant

A part of the cell culture obtained by Example 5-(2) was centrifuged at 1,750×g, at 4° C., for 10 minutes to collect a supernatant. The supernatant is referred to as an insect cell culture supernatant.

(4) PEG Precipitation

The insect cell culture supernatant obtained by Example 5-(3) was put in two tubes (7 mL/tube). Into one tube, a 40% PEG-6,000 solution was added so that the final concentration of PEG became 8%, and mixed. The mixture was left standing on ice for 30 minutes, and then centrifuged at 1,500×g, at 4° C., for 30 minutes to collect a pellet. The pellet was suspended in 140 μL of DPBS. The suspension wad left standing at 4° C. overnight to dissolve the pellet. The solution thus obtained is referred to as sample (8% PEG precipitation). Into the other tube, a 40% PEG-6000 solution (dissolved in DPBS) was added so that the final concentration of PEG became 2%, and mixed. The mixture was left standing on ice for 30 minutes, and then centrifuged at 1,500×g, at 4° C., for 30 minutes to collect a supernatant. To the supernatant, a 40% PEG-6000 solution was added so that the final concentration of PEG became 8%, and mixed. The mixture was left standing on ice for 30 minutes, and then centrifuged at 1,500×g, at 4° C., for 30 minutes to collect a pellet. The pellet was suspended in 140 μL of DPBS. The suspension wad left standing at 4° C. overnight to completely dissolve the pellet. The solution thus obtained is referred to as sample (2-8% PEG precipitation).

(5) Determination of Genomic Titer

The genomic titer of the samples obtained by Example 5-(4) was determined in the same manner as Example 1-(5). As a result, the genomic titer of the 8% PEG precipitation and the genomic titer of the 2-8% PEG precipitation were almost equal.

(6) Determination of Protein Purity

Figure 5:
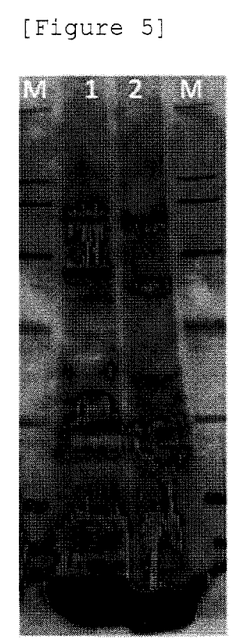
FIG. 5 An SDS-PAGE photograph of culture supernatants of insect cells treated with two-staged PEG concentration.

The purity of the samples obtained by Example 5-(4) was determined in the same manner as Example 1-(6). Results are shown in FIG. 5. In FIG. 5, each lane is as follows: lane 1: 8% PEG precipitation, lane 2: 2-8% PEG precipitation, M: molecular-weight marker.

As seen from FIG. 5, the 2-8% PEG precipitation (lane 2) had a smaller number of bands than the 8% PEG precipitation (lane 1). These results show that impurities in a culture supernatant of an insect cell can be removed by PEG precipitation. Considering the results of Example 5-(5), it was found that a rAAV particle can be purified by PEG precipitation.

INDUSTRIAL APPLICABILITY

According to the method of producing a non-enveloped virus of the present invention, a non-enveloped virus particle with high purity can be obtained without laborious operations. A non-enveloped virus particle produced by the production method of the present invention and a composition comprising the non-enveloped virus particle as an active ingredient are very useful in gene transfer methods in the fields of basic research study and clinical application for gene therapy.

The invention claimed is:

1. A method of producing a non-enveloped virus particle, the method comprising:
    (a) a step of treating a sample containing a non-enveloped virus particle with a first concentration of polyethylene glycol (PEG),
    (b) a step of removing a precipitate produced in step (a) and treating a supernatant with a second concentration of PEG, and
    (c) a step of obtaining a non-enveloped virus particle from a precipitate produced in step (b),
    wherein the non-enveloped virus is adeno-associated virus, and the second concentration of PEG is higher than the first concentration of PEG.

2. The method according to claim 1, wherein the first concentration of PEG is 0.5 to 4%.

3. The method according to claim 1, wherein the second concentration of PEG is 3 to 10%.

4. The method according to claim 1, wherein the sample containing a non-enveloped virus particle is a crude extract obtained by bringing a non-enveloped virus-producing cell into contact with an acidic solution.

5. The method according to claim 1, wherein the sample containing a non-enveloped virus particle is a sample treated with nuclease.

6. The method according to claim 1, wherein the sample containing a non-enveloped virus particle is a sample treated with chloroform.

7. The method according to claim 1, wherein the sample containing a non-enveloped virus particle is a crude extract obtained by bringing a non-enveloped virus-producing cell into contact with an acidic solution and then treated with an acid.

8. The method according to claim 1, which comprises a step of treatment with chloroform after the step (c).

9. The method according to claim 4, wherein the acidic solution contains a cation and citric acid.

10. The method according to claim 1, wherein the first concentration of PEG is 0.5 to 4%, and the second concentration of PEG is 3 to 10%.

* * * * *